United States Patent

Katano et al.

Patent Number: 5,814,636
Date of Patent: Sep. 29, 1998

[54] COMPOUNDS WITH PLATELET AGGREGATION INHIBITOR ACTIVITY

[75] Inventors: Kiyoaki Katano; Shokichi Ohuchi; Tomoaki Miura; Eiki Shitara; Masaro Shimizu; Kazue Yaegashi; Naoto Ohkura; Yasuko Isomura; Hiroyuki Iida; Midori Ishikawa; Kenji Asai; Emiko Hatsushiba, all of Kanagawa-ken, Japan

[73] Assignee: Meiji Seika Kabushiki Kaisha, Tokyo-to, Japan

[21] Appl. No.: 615,227

[22] PCT Filed: Jul. 17, 1995

[86] PCT No.: PCT/JP95/01419

§ 371 Date: Jul. 10, 1996

§ 102(e) Date: Jul. 10, 1996

[87] PCT Pub. No.: WO96/02503

PCT Pub. Date: Feb. 1, 1996

[30] Foreign Application Priority Data

Jul. 15, 1994 [JP] Japan .................................. 6-163506
Jun. 2, 1995 [JP] Japan .................................. 7-135514

[51] Int. Cl.[6] ...................... A61K 31/495; A61K 31/445; C07D 401/04; C07D 401/14
[52] U.S. Cl. ......................... 514/252; 514/316; 544/360; 544/364; 546/187; 546/188; 546/189; 546/190
[58] Field of Search ..................... 544/360, 364; 514/252, 316; 546/187, 188, 189, 190

[56] References Cited

U.S. PATENT DOCUMENTS

| | | | |
|---|---|---|---|
| 5,225,402 | 7/1993 | Ogawa et al. | 514/23 |
| 5,273,982 | 12/1993 | Alig et al. | 514/315 |
| 5,442,004 | 8/1995 | Pieper et al. | 544/360 |
| 5,700,801 | 12/1997 | Pieper et al. | 514/252 |

FOREIGN PATENT DOCUMENTS

| | | |
|---|---|---|
| 0 503 548 A1 | 9/1992 | European Pat. Off. . |
| 0 528 369 A2 | 2/1993 | European Pat. Off. . |
| 0 542 363 A3 | 5/1993 | European Pat. Off. . |
| 0 604 800 A1 | 7/1994 | European Pat. Off. . |
| 0 638 553 A1 | 2/1995 | European Pat. Off. . |
| 3-173870 | 7/1991 | Japan . |
| 1278166 | 6/1972 | United Kingdom . |

OTHER PUBLICATIONS

Pieper et al, *Chemical Abstracts*, vol. 125, No. 142565 (Abstract for DE 4,446,301, Jun. 27, 1996).

Pieper et al, *Chemical Abstracts*, vol. 125, No. 195688 (Abstract for WO 9620,173, Jul. 4, 1996).

*Primary Examiner*—Emily Bernhardt
*Attorney, Agent, or Firm*—Wenderoth, Lind & Ponack, L.L.P.

[57] ABSTRACT

A compound represented by the general formula (I) and a pharmaceutically acceptable salt and solvate thereof having an effect for inhibiting the aggregation of platelets is disclosed:

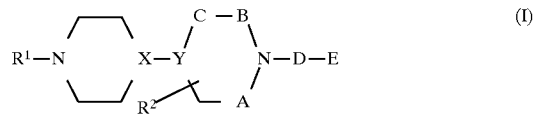

wherein

A, B and C represent independently $CH_2$ or $C=O$;

X and Y are different from each other, and each of them is CH or N;

D is $-(CH_2)_k-$ or $-(CH_2)_m-CO-$ where k is an integer of 1 to 4; and m is an integer of 0 to 3;

E is the following group (II) or (III):

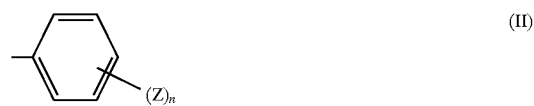

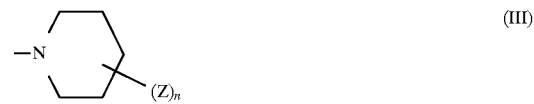

wherein n is an integer of 1 to 3; and Z is $-W-(CH_2)_p-COOR^3$ (wherein W is $-O-$ or a bond; p is an integer of 1 to 4; and $R^3$ is hydrogen, lower alkyl or an ester residue which can be removed under physiological conditions); $R^1$ is hydrogen or lower alkyl; and $R^2$ is hydrogen atom or lower alkyl.

10 Claims, No Drawings

COMPOUNDS WITH PLATELET AGGREGATION INHIBITOR ACTIVITY

BACKGROUND OF THE INVENTION

1. Field of the Invention

The present invention relates to nitrogen-containing heterocyclic derivatives for inhibiting the aggregation of platelets, and pharmaceutical compositions for the treatment and prophylaxis of thrombotic diseases comprising as effective ingredient at least one of these derivatives.

2. Description of Related Art

Cardiovascular diseases are increased along with the change of dietary habits and the increase of advanced ages. Almost fifty percent of these diseases may be caused by thrombus.

Platelets in plasma are mainly associated with the formation of thrombus in organisms. For the purpose of the treatment and prophylaxis of thrombotic diseases in clinical practice, there have been used a medicine which suppresses the functions of platelet or inhibits the aggregation of platelets, for example, aspirin which inhibits cyclooxygenase and ticlopidine which activates adenylcyclase.

In recent years, glycoproteins on platelet membrane have been progressively analyzed. As the results, it has been elucidated that the glycoprotein called GPIIb/IIIa is a receptor of fibrinogen. This has therefore led to the expectation that a GPIIb/IIIa antagonists would become an inhibitor of platelet aggregation having a novel action mechanism effectively used for the treatment and prophylaxis of the thrombotic diseases (Trends in Pharmacological Science, 13, 413, 1992). The compounds as the GPIIb/IIIa antagonist include monoclonal antibodies (Ann. New York Acad. Sci., 614, 193, 1991), tripeptide derivatives comprising arginine-glycine-aspartic acid (J. Med. Chem., 35, 2040, 1992), amidinophenyl derivatives (J. Med. Chem., 35, 4393, 1992; Japanese Patent Laid-Open Publication Nos. 264068/1992, 334351/1992, EP-483667, EP-502536, EP-525629, EP-29858, EP-537980, WO-9307867 and WO-9402472), tyrosine derivatives (J. Med. Chem., 35, 4640, 1992), and piperidine derivatives (EP-512831, EP-540334 and EP-578535).

It is also desired to be developed a drug having no side effects such as hemorrhage and a highly selective function as a therapeutic or prophylactic agent of thrombotic diseases.

SUMMARY OF THE INVENTION

The present inventors have now found that a certain kind of a compound becomes a GPIIb/IIIa antagonist.

Thus, an object of the present invention is to provide novel compounds inhibiting the aggregation of platelets.

Another object of the present invention is to provide a pharmaceutical composition comprising a novel compound having the above effect.

Further object of the present invention is to provide a therapeutic or prophylactic method of thrombotic diseases which comprises administering a novel compound having the above activity.

Further object of the present invention is to provide the use of the novel compound having the above activity for preparing a pharmaceutical composition used for the therapy or prophylaxis of thrombotic disorders.

The compound according to the present invention is represented by the formula (I):

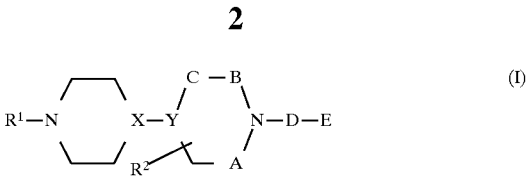

or a pharmaceutically acceptable salt and solvate thereof, wherein

A, B and C independently represent $CH_2$ or $C=O$;

X and Y are different from each other, and each of them is CH or N;

D is —$(CH_2)_k$— or —$(CH_2)_m$—CO— (wherein k is an integer of 1 to 4; and m is an integer of 0 to 3);

E is the following group (II) or (III)

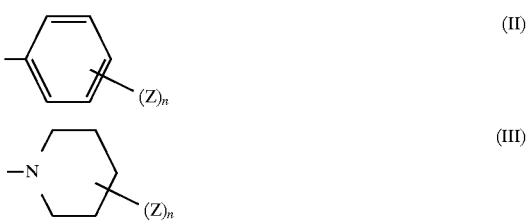

wherein n is an integer of 1 to 3; and Z is —W—$(CH_2)_p$—$COOR^3$ (wherein W is —O— or a bond; p is an integer of 1 to 4; and $R^3$ is hydrogen, lower alkyl or an ester moiety which can be removed under physiological conditions);

$R^1$ is hydrogen or lower alkyl in which at least one hydrogen atom may be substituted by hydroxyl, halogen, amino, lower alkylamino, or imino, or a lower-alkyl-substituted-2-oxodioxol-4-yl group;

$R^2$ is hydrogen; lower alkyl in which at least one hydrogen atom may be substituted by hydroxyl, halogen, amino, carboxyl, lower alkoxy, lower alkylamino or lower alkoxycarbonyl; phenyl in which at least one hydrogen atom may be substituted by hydroxyl, halogen, amino, carboxyl, lower alkoxy, lower alkylamino, lower alkoxycarbonyl or halo-lower alkyl; or phenyl-lower alkyl in which at least one hydrogen atom of this phenyl group may be substituted by hydroxyl, halogen, amino, carboxyl, lower alkoxy, lower alkylamino, lower alkoxycarbonyl or halo-lower alkyl.

DETAILED DESCRIPTION OF THE INVENTION

Compound of the formula (I)

The term "lower alkyl" as a group or a portion of a group herein means a straight or branched alkyl chain having 1 to 6, preferably 1 to 4 carbon atoms. The term halogen atom means fluorine, chlorine, bromine or iodine. Furthermore, the term "haloalkyl" means an alkyl group in which one or more hydrogen atoms are substituted by halogen atoms.

In the formula (I), A, B and C each is $CH_2$ or $C=O$. According to a preferable embodiment of the present invention, a compound in which A is $C=O$ and the others are the $CH_2$ groups is preferable. According to another embodiment, a compound in which two of A, B and C are the $C=O$ groups and the other is $CH_2$ is preferable.

In the formula (I), X and Y are different from each other, and each of them is CH or N. A compound in which X is CH and Y is N is preferable.

In the formula (I), D is —$(CH_2)_k$— (wherein k is an integer of 1 to 4, preferably 1 or 2) or —$(CH_2)_m$—CO— (wherein m is an integer of 0 to 3, preferably 1 to 3, more preferably 1 or 2). D is preferably —$(CH_2)_m$—CO—, and more preferably, it is —$CH_2$—CO—.

E is the group (II) or (III). In the group (II) or (III), n is preferably 1 or 2. That is, the number of the substituent Z is preferably 1 or 2. The position of the substituent Z is preferably a para-position or a meta-position to the position of D.

In the group —W—(CH$_2$)$_p$—COOR represented by Z, W is preferably —O—, p is preferably 1 or 2, and R$^3$ is preferably a hydrogen atom or C$_{1-4}$ alkyl (e.g., methyl, ethyl, n-propyl, iso-propyl, n-butyl, iso-butyl, sec-butyl or tert-butyl). Preferable examples of an ester residue represented by R$^3$ which can be removed under physiological conditions include pivaloyloxymethyl, 1-(cyclohexyloxycarbonyloxy) ethyl and (5-methyl-2-oxo-1,3-dioxol-4-yl)methyl.

In the formula (I), R$^1$ is a hydrogen atom or a lower alkyl group. At least one hydrogen atom of the lower alkyl group may be substituted. Preferred examples of this substituent include a hydroxyl group, a halogen group (preferably, chlorine, bromine or fluorine), an amino group, a lower alkylamino group (preferably, methylamino, ethylamino, propylamino, dimethylamino or diethylamino), an imino group or 5-lower alkyl group-substituted-2-oxodioxol-4-yl.

R$^2$ is a hydrogen atom, a lower alkyl group, a phenyl group or a phenyl-lower alkyl group. At least one hydrogen atom of this lower alkyl group may be substituted. Preferred examples of this substituent include a hydroxyl group, a halogen atom (preferably, chlorine, bromine or fluorine), an amino group, a carboxyl group, a lower alkoxy group (preferably, methoxy, ethoxy, n-propoxy or iso-propoxy), a lower alkylamino group (preferably, methylamino, ethylamino, propylamino, dimethylamino or diethylamino), or a lower alkoxycarbonyl group (preferably, methoxycarbonyl, ethoxycarbonyl, n-propoxycarbonyl or iso-propoxycarbonyl). Furthermore, at least one hydrogen atom of the phenyl group may be may be substituted. Preferred examples of this substituent include a hydroxyl group, a halogen atom (preferably, chlorine, bromine or fluorine), an amino group, a carboxyl group, a lower alkoxy group (preferably, methoxy, ethoxy, n-propoxy or iso-propoxy), a lower alkylamino group (preferably, methylamino, ethylamino, propylamino, dimethylamino or diethylamino), a lower alkoxycarbonyl group (preferably, methoxycarbonyl, ethoxycarbonyl, n-propoxycarbonyl or iso-propoxycarbonyl), or a halo-lower alkyl group (preferably, trifluoromethyl or trifluoroethyl). In addition, at least one hydrogen atom of the phenyl moiety of the phenyl-lower alkyl group (preferably, benzyl, 2-phenylethyl or 3-phenylpropyl) may be substituted. Preferred examples of this substituent include a hydroxyl group, a halogen atom (preferably, chlorine, bromine or fluorine), an amino group, a carboxyl group, a lower alkoxy group (preferably, methoxy, ethoxy, n-propoxy or iso-propoxy), a lower alkylamino group (preferably, methylamino, ethylamino, propylamino, dimethylamino or diethylamino), a lower alkoxycarbonyl group (preferably, methoxycarbonyl, ethoxycarbonyl, n-propoxycarbonyl or iso-propoxycarbonyl), or a halo-lower alkyl group (preferably, trifluoromethyl or trifluoroethyl).

Preferred examples of the compound represented by the formula (I) include:

[[4-[[4-(piperidin-4-yl)-2-oxopiperazin-1-yl]acetyl]-o-phenylene]dioxy]diacetic acid,
[[4-[[4-(piperidin-4-yl)piperazin-1-yl]acetyl]-o-phenylene]dioxy]diacetic acid,
4-[[4-(piperidin-4-yl)-2-oxopiperazin-1-yl]acetyl] phenoxyacetic acid,
diethyl [[4-[[4-(piperidin-4-yl)-2-oxopiperazin-1-yl]acetyl]-o-phenylene]dioxy]diacetate,
n-butyl 4-[[4-(piperidin-4-yl)-2,6-dioxopiperazin-1-yl] acetyl]phenoxyacetate,
4-[[4-(piperidin-4-yl)-2,6-dioxopiperazin-1-yl]acetyl] phenoxyacetic acid,
n-butyl 4-[[4-(piperidin-4-yl)-2,3-dioxopiperazin-1-yl] acetyl]phenoxyacetate,
4-[[4-(piperidin-4-yl)-2,3-dioxopiperazin-1-yl]acetyl] phenoxyacetic acid,
n-butyl 4-[[4-(piperidin-4-yl)-2,5-dioxopiperazin-1-yl] acetyl]phenoxyacetate,
4-[[4-(piperidin-4-yl)-2,5-dioxopiperazin-1-yl]acetyl] phenoxyacetic acid,
n-butyl 4-[[4-(piperidin-4-yl)-2-oxopiperazin-1-yl]acetyl] phenoxyacetate.dihydrochloride and
ethyl 4-[[4-(piperidin-4-yl)-2-oxopiperazin-1-yl]acetyl] phenoxyacetate.

The compound according to the present invention can be in the form of a salt. Such a salt includes a pharmacologically acceptable non-toxic salt. Preferred examples of the salt include inorganic salts such as a sodium salt, a potassium salt, a magnesium salt and a calcium salt, acid addition salts such as a trifluoroacetate salt, a hydrochloride salt, an oxalate salt and a methanesulfonate salt a citrate salt, and amino acid salts such as a glutamate salt and an aspartate salt.

The compound according to the present invention can be in the form of a solvate. The solvate preferably includes a hydrate and an ethanolate.

Preparation of the Compound represented by the Formula (I)

The compound according to the present invention can be prepared by the following processes.

Protective groups for an amino group which are generally used in peptide synthesis may be used in the following processes. Preferred examples of the protective group include t-butoxycarbonyl, benzyloxycarbonyl, p-methoxybenzyloxycarbonyl, 2,2,2-trichloroethoxycarbonyl, trifluoroacetyl, allyloxycarbonyl and trityl. Furthermore, protective groups for a carboxyl group which are generally used in peptide synthesis may be used in the following processes. Preferred examples of the protective group include methyl, ethyl, tert-butyl, benzyl, p-methoxybenzyl, p-nitrobenzyl, allyl and benzhydryl.

Process (A)

A compound represented by the formula (I) in which X is CH and Y is N can be prepared in accordance with the following steps in Scheme A.

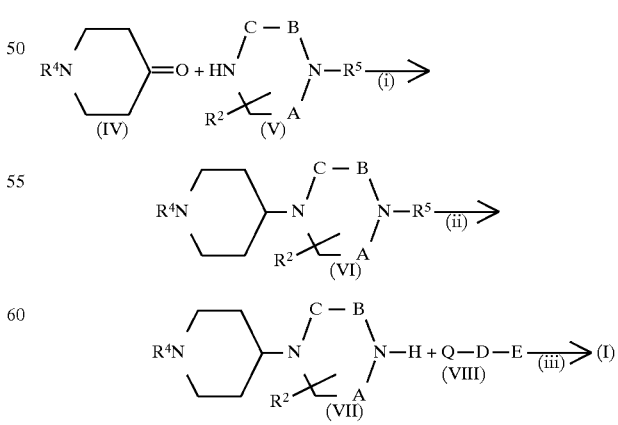

Scheme A wherein
R$^4$ is R$^1$ or a protected amino group, $R^5$ is a hydrogen atom or a protective group for the amino group, but it is different from $R^4$, Q is a halogen atom (e.g., chlorine, bromine or iodine), a lower alkylsulfonyloxy group (e.g., methanesulfonyloxy), trifluoromethanesulfonyloxy or an arylsulfonyloxy group (e.g., p-toluenesulfonyloxy), and A, B, C, $R^2$, D, Z and n are as defined above.

In the step (i), the compound of the formula (IV) and the compound of the formula (V) are subjected to a reductional alkylation in an inert solvent (e.g., THF, dichloromethane, 1,2-dichloroethane, dioxane or DMF) to obtain the compound of the formula (VI). In this reductional alkylation, a metal hydride reagent such as cyanoboronsodium hydride, cyanoboronlithium hydride, boronsodium hydride, boronlithium hydride and triacetoxyboronsodium hydride can be used. A catalytic reduction with a catalyst such as palladium-carbon, palladium black, palladium hydroxide, platinum oxide and a Raney nickel catalyst can be also use. The reaction can be carried out at −20° to 100° C., preferably 0° to 70° C. for 0.5 to 48 hours, preferably 1 to 24 hours.

When $R^5$ in the compound of the formula (VI) is the protective group for the amino group, this protective group is removed in the step (ii).

In the step (iii), the compound of the formula (I) is prepared by reacting the compound of the formula (VII) with the compound of the formula (VIII) in the presence of a base in an inert solvent (e.g., THF, toluene, xylene, 1,2-dichloroethane, DMF or dioxane), and if necessary, removing the protective group. Examples of the base include metallic sodium, sodium hydride, calcium hydride, lithium hydride, sodium amide, potassium carbonate, sodium hydroxide, potassium hydroxide, n-butyllithium and lithiumdiisopropyl amide. If necessary, an interphase transfer catalyst (e.g., a tetraalkylammonium halide) may be used together with the base. The reaction can be carried out at −80° to 150° C., preferably −50° to 120° C. for 0.5 to 72 hours, preferably 0.5 to 36 hours.

The compound represented by the formula (V) can be synthesized in accordance with the procedure described in Bull. Chem. Soc. Jap., Vol. 46, p. 3612 (1973) and EP 529858.

Process (B)

A compound represented by the formula (I) in which X is N and Y is CH can be prepared in accordance with the following steps of Scheme B.

Scheme B

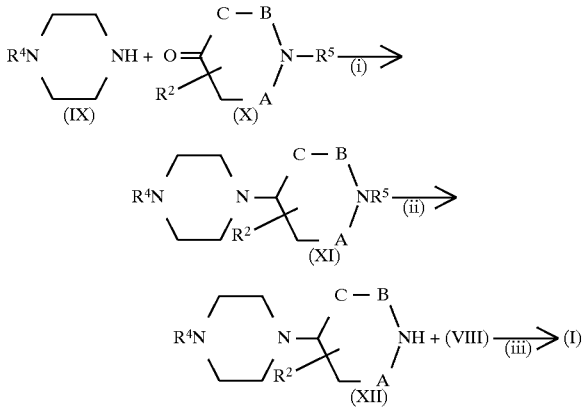

wherein $R^4$ and $R^5$ are as defined above, and A, B, C and $R^2$ are also as defined above. The reaction of the compound of the formula (IX) with the compound of the formula (X) in the step (i) can be carried out under the same conditions as in the step (i) of the scheme A. Furthermore, the reactions of the steps (ii) and (iii) can be carried out by the same procedure as in the reactions of the steps (ii) and (iii) of the scheme A.

Process (C)

A compound represented by the formula (I) in which Z is the group (III) can be prepared in accordance with the following steps of Scheme C.

Scheme C

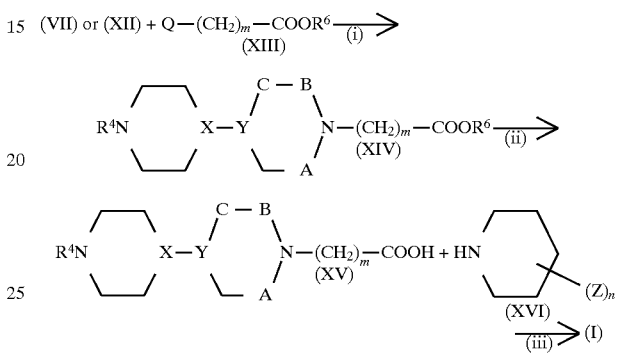

wherein $R^6$ is $R^3$ or a protective group for a carboxyl group,

A, B, C, m, Z and n are as defined in the formula (I), and $R^4$ is as defined in the scheme A.

In the step (i), the reaction of the compound of the formula (VII) or the compound of the formula (VII) with the compound of the formula (VIII) can be carried out in the presence of a base by the same procedure as in the reaction of the step (iii) of the scheme A.

When $R^6$ in the obtained compound of the formula (XIV) is the protective group for the carboxyl group, this protective group is removed in the step (ii).

In the step (iii), the compound of the formula (XV) is reacted with the compound of the formula (XVI) in the presence of a carboxylic acid activating agent to form an amide bond. Examples of the carboxylic acid activating agent include thionyl chloride, phosphorus oxychloride, dicyclohexyl carbodiimide, 1-hydroxybenzotriazole, benzotriazol-1-yloxy-tris(dimethylamino)phosphonium and hexafluorophosphate.

Process (D)

A compound represented by the formula (I) in which X is CH, Y is N, A and B each is C=O and C is $CH_2$ can be prepared in accordance with the following steps in Scheme D.

Scheme D

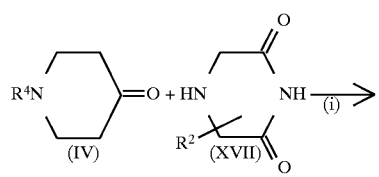

-continued
Scheme D

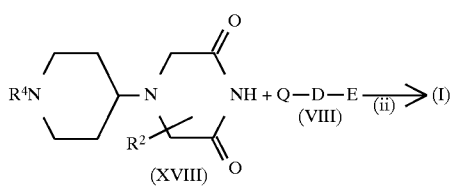

wherein R⁴ is as defined in the scheme A.

In the step (i), the compound of the formula (IV) and the compound of the formula (XVII) are subjected to a reductional alkylation in the presence or absence of an acid in an inert solvent (e.g., THF, dichloromethane, 1,2-dichloroethane, dioxane or DMF) to obtain the compound of the formula (XVIII). The reductional alkylation reagents which can be used in the step (i) of the scheme A can also used in this process. The reaction can be carried out at −20° to 100° C., preferably 0° to 70° C. for 0.5 to 48 hours, preferably 1 to 24 hours.

In the step (ii), the compound of the formula (I) is prepared by reacting the compound of the formula (XVIII) with the compound of the formula (VIII) in the presence of a base in an inert solvent (e.g., DMF, acetone, acetonitrile, dichloromethane, THF or dioxane), and if necessary, removing the protective group. The bases which can be used in the step (iii) of the scheme A can also be used in this process. The reaction can be carried out at −78° to 100° C., preferably −30° to 50° C. for 0.5 to 48 hours, preferably 0.5 to 12 hours.

The compound represented by the formula (XVII) can be synthesized in accordance with the procedure described in J. Chem. Soc., p. 3874 (1953).

Process (E)

A compound represented by the formula (I) in which X is CH, Y is N, A is CH, and B and C each is C=O can be prepared in accordance with the following steps in Scheme E.

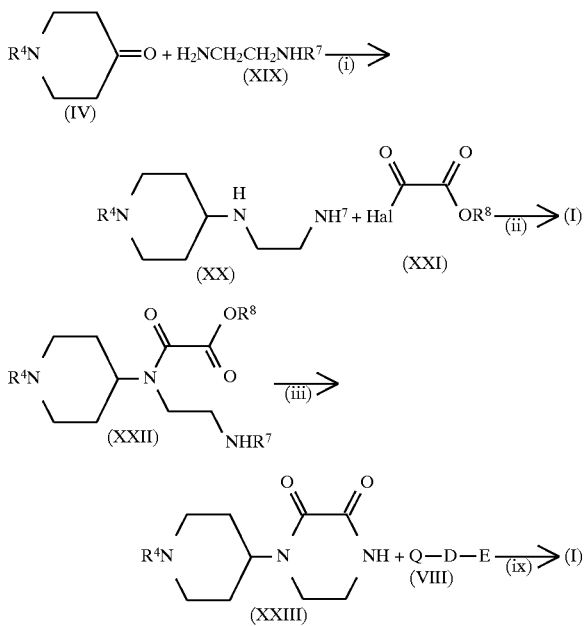

wherein

R⁷ is a protective group for an amino group,

R⁸ is a hydrogen atom or a lower alkyl group (e.g., methyl, ethyl, n-propyl or n-butyl), Hal is a halogen atom (e.g., chlorine, bromine or iodine), and R⁴ is as defined in the scheme A.

In the step (i), the reaction of the compound of the formula (IV) and the compound of the formula (XIX) can be carried out by the same procedure as in the step (i) of the scheme D.

In the step (ii), the compound of the formula (XX) is reacted with the compound of the formula (XXI) in the presence or absence of a base in an inert solvent (e.g., dichloromethane, THF, dioxane or acetonitrile) to obtain the compound of the formula (XXII). Examples of the base which can be used in this reaction include pyridine, triethylamine, N-methylmorpholine and dimethylaminopyridine. The reaction can be carried out at −50° to 100° C., preferably −20° to 80° C. for 10 minutes to 24 hours, preferably 10 minutes to 12 hours.

In the step (iii), the compound of the formula (XXII) is cyclized with removing the protective group for the amino group to give the compound of the formula (XXIII). The reaction can be carried out at −20° to 100° C., preferably 0° to 80° C. for 0.5 to 48 hours, preferably 1 to 24 hours.

The thus obtained compound of the formula (XXIII) can then be reacted with the compound of the formula (VIII) by the same procedure as in the above step (i) to obtain the compound of the formula (I).

The compound of the formula (XIX) can be synthesized in accordance with the procedure described in Synthesis, p. 1032 (1984).

Process (F)

A compound represented by the formula (I) in which X is CH, Y is N, A and B each is C=O, and B is CH can be prepared in accordance with the preparation process of the following steps in Scheme F.

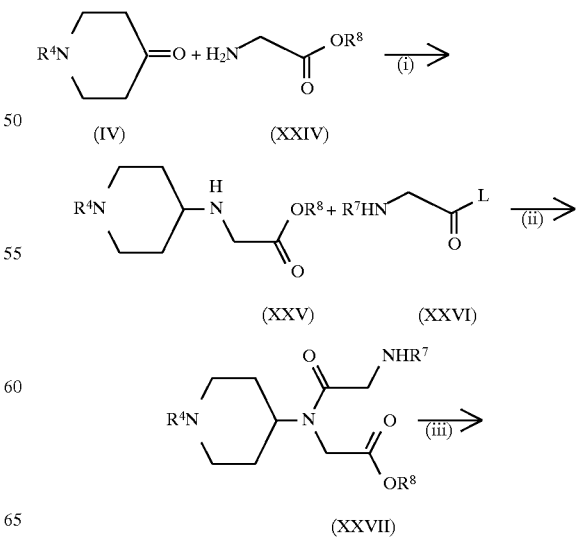

-continued
Scheme F

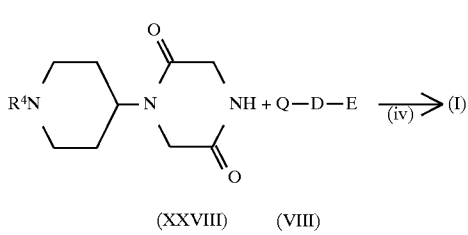

(XXVIII)    (VIII)

wherein L is a halogen atom (e.g., chlorine, bromine or iodine), a lower alkylsulfonyloxy group (e.g., methanesulfonyloxy) or an arylsulfonyloxy group (e.g., p-toluenesulfonyloxy), and $R^7$ and $R^8$ are as defined in the scheme E.

In the step (i), the reaction of the compound of the formula (IV) and the compound of the formula (XXIV) can be carried out by the same procedure as in the step (i) of the scheme D.

In the step (ii), the compound of the formula (XXV) is reacted with the compound of the formula (XXVI) in the presence or absence of a base in an inert solvent (e.g., DMF, dichloromethane, acetonitrile, THF or dioxane) to obtain the compound of the formula (XXVII). Examples of the base which can be used in this reaction include those which can be used in the step (iii) of the scheme A. The reaction can be carried out at −20° to 100° C., preferably 0° to 80° C. for 0.5 to 48 hours, preferably 1 to 24 hours.

The compound of the formula (XXVII) can be reacted by the same procedure as in the step (iii) of the scheme E to obtain the compound of the formula (XXVIII).

The thus obtained compound of the formula (XXIII) can then be reacted with the compound of the formula (VIII) by the same procedure as in the step (iv) of the scheme E to obtain the compound of the formula (I).

In each process described above, it is apparent to a person skilled in the art that the order of the synthesis can be decided so that any side reaction may not occur on functional groups which are not concerned with the reactions, and the functional groups can be protected by suitable protective groups so that an unpreferable reaction may not proceed.

Use of the compound/pharmaceutical composition

The compound according to the present invention inhibits the aggregation of platelets by inhibiting the binding of platelet membrane protein GPIIb/IIIa and fibrinogen. Thus, the compound according to the present invention and a pharmacologically acceptable salt thereof are effective in the treatment and prophylaxis of thrombotic disorders caused by the aggregation of platelets, particularly cerebral infarction, myocardial infarction, angina pectoris or peripheral arteriocclusion.

A pharmaceutical composition comprising the compound according to the present invention or a pharmacologically acceptable salt thereof as effective ingredients can be administered human and non-human animal subjects through any one of routes such as oral or parenteral routes such as intravenous injection, intramuscular injection, subcutaneous administration, rectal administration or percutaneous administration.

Therefore, the pharmaceutical composition comprising the compound according to the present invention is processed into suitable dosage forms depending on dosage routes, and can be specifically formed into preparations mainly including injections such as intravenous injection or intramuscular injection, oral preparations such as capsule, tablet, granule, powder, pill, grains or troche, rectal preparations, oily suppositories or aqueous suppositories.

These preparations can be prepared in the usual manners with conventional additives such as an excipient, a filler, a binder, a humidifier, a disintegrating agent, a surface active agent, a lubricant, a dispersant, a buffer, a preservative, a dissolution aid, an antiseptic agent, a flavoring agent, an analgesic agent or a stabilizer. The aforementioned acceptable and non-toxic additives include, for example, lactose, fructose, glucose, starch, gelatin, magnesium carbonate, synthetic magnesium silicate, talc, magnesium stearate, methyl cellulose or a salt thereof, gum arabic, polyethylene glycol, syrup, vaseline, ethanol, propylene glycol, citric acid, sodium chloride, sodium sulfite and sodium phosphate.

The compound according to the present invention in a pharmaceutical composition is contained in amounts depending on its dosage forms, which generally range from about 1 to 70% by weight, preferably from about 5 to 50% by weight of the total composition.

The dose is appropriately determined in consideration of the use, and the age, sex and severity of a patient. The dose is generally in the range from about 0.1 to 1,000 mg, preferably from 1 to 200 mg per day to an adult patient for the purpose of the treatment of thrombotic disorders. The dose may be administered in one or more portions per day.

The present invention will be described in more detail with reference to examples, but the scope of the present invention should not be limited to these examples.

EXAMPLE 1

[[4-[[4-(piperidin-4-yl)-2-oxopiperazin-1-yl]acetyl]-o-phenylene]dioxy]diacetic acid trifluoroacetate (a) A mixture of 1-t-butoxycarbonyl-4-oxopiperidine (2.985 g) and 2-oxopiperazine (1.5 g) was dissolved in methanol (25 ml), and molecular sieves 3A (2.5 g) and 1N ethanol-hydrochloric acid (2.5 ml) were then added, followed by stirring for 45 minutes. Cyanoboronsodium hydride (945 ml) was divided into three portions and they were then separately added to the solution under ice-cooling, followed by stirring 5 hours at room temperature. After insolubles were removed with sellaite, the filtrate was then concentrated. To the resultant residue, a saturated sodium hydrogencarbonate solution was added, and extracted with ethyl acetate. The ethyl acetate layer was washed with a saturated saline solution and then dried over magnesium sulfate. After the solvent was evaporated, the residue was purified by silica gel column chromatography (300 g, chloroform:methanol=30:1 to 10:1) to give 1.448 g of 4-(1-t-butoxycarbonylpiperidin-4-yl)-2-oxopiperazine.

$^1$H-NMR (CDCl$_3$) δ: 1.42 (2H, m), 1.46 (9H, s), 1.80 (2H, brd), 2.46 (1H, tt, J=3.6, 11.2 Hz), 2.7–2.8 (4H), 3.27 (2H, s), 3.35 (2H, td, J=3.0, 5.2 Hz), 4.12 (2H, brs), 6.06 (1H, s).

EIMS (m/z): 283 (M$^+$)

(b) A mixture of sodium (35 mg) and toluene (10 ml) was heated up to a temperature of 110° to 120° C., and then sufficiently stirred to make sodium particulate. Then, the compound (430 mg) obtained in the above (a) was added thereto, and the solution was then heated under reflux for 3 hours. After cooling to about 60° C., di-t-butyl [(4-chloroacetyl-o-phenylene)dioxyl diacetate (1 g) was added, and the solution was heated under reflux for 3 hours. After cooling, the reaction solution was diluted with ethyl acetate, washed with water, and then dried over magnesium sulfate. After the solvent was evaporated, the residue was purified by silica gel column chromatography (50 g, chloroform:methanol=50:1) to give 116 mg of di-t-butyl [[4-[[4-(1-t-butoxycarbonylpiperidin-4-yl)-2-oxopiperazin-1-yl]acetyl]-o-phenylene]dioxy]diacetate.

$^1$H-NMR (CDCl$_3$) δ: 1.46 (9H, s), 1.47 (9H, s), 1.48 (9H, s), 1.65 (2H, m), 1.82 (2H, brd), 2.47 (1H, m), 2.75 (2H, m), 2.84 (2H, m), 3.36 (4H, m), 4.13 (2H, brs), 4.64 (2H, s), 4.68 (2H, s), 4.76 (2H, s), 6.82 (1H, d, J=8.3 Hz), 7.48 (1H, d, J=1.9 Hz), 7.60 (1H, dd, J=1.9, 8.3 Hz).

EIMS (m/z): 661 (M$^+$)

(c) The compound (115 mg) obtained in the above (b) was added to a mixture of trifluoroacetic acid (1.5 ml) and anisole (0.1 ml), and reaction was then carried out at room temperature for 2 hours. Diisopropyl ether (10 ml) was added thereto under ice-cooling, and the resultant precipitate was collected by filtration, and then dried to give 111 mg of the title compound.

$^1$H-NMR (D$_2$O+Na$_2$CO$_3$) δ: 1.61 (2H, q, J=3.3 Hz), 2.15 (2H, brd), 2.78 (1H, brt), 2.90 (2H, brt), 3.04 (2H, m), 3.39–3.51 (6H), 4.64 (2H, s), 4.68 (2H, s), 4.97 (2H, s), 7.01 (1H, d, J=8.4 Hz), 7.45 (1H, s), 7.74 (1H, d, J=8.4 Hz).

SIMS (m/z): 450 (M$^+$+1)

EXAMPLE 2

[[1-[4-(piperidin-4-yl)-2-oxopiperazin-1-yl]acetyl] piperidin-4-yl]oxyacetic acid trifluoroacetate (a) The same procedure as in Example 1(b) was repeated except that di-t-butyl [(4-chloroacetyl-o-phenylene)dioxy] diacetate was replaced with ethyl bromoacetate to give ethyl [4-(1-t-butoxycarbonylpiperidin-4-yl)-2-oxopiperazin-1-yl] acetate.

$^1$H-NMR (CDCl$_3$) δ: 1.28 (3H, t, J=7.2 Hz), 1.40 (2H, m), 1.46 (9H, s), 1.80 (2H, brd), 2.45 (1H, m), 2.74 (2H, brt), 2.82 (2H, brt), 3.33 (2H, s), 3.39 (2H, t, J=5.4 Hz), 4.12 (2H, s), 4.20 (2H, q, J=7.2 Hz).

EIMS (m/z): 369 (M$^+$)

(b) The compound (360 mg) prepared in the above (a) was dissolved in 5 ml of ethanol, and a 1N sodium hydroxide solution (1.5 ml) was added, followed by stirring at room temperature for 3 hours. After the reaction solution was concentrated, water was added, and the pH of the solution was adjusted to 4.0 with 1N hydrochloric acid. The solution was then lyophilized to give [4-(1-t-butoxycarbonylpiperidin-4-yl)-2-oxopiperazin-1-yl]acetic acid hydrochloride (349 mg). This product was used in a subsequent reaction without purification.

$^1$H-NMR (D$_2$O) δ: 1.46 (9H, s), 1.60 (2H, qd, J=4.3, 12.6 Hz), 2.12 (2H, brd), 2.87 (2H, brt), 3.42 (1H, brt), 3.55 (2H, brt), 3.67 (2H, brt), 3.89 (2H, s), 4.00 (2H, s), 4.18–4.27 (2H, brs).

(c) The compound (151 mg) prepared in the above (b) was dissolved in methylene chloride (3 ml), and 1-hydroxybenzotriazole and benzotriazole-1-yloxy-tris (dimethylamino)phosphonium hexafluorophosphate (195 mg) were added to the solution, followed by stirring for 50 minutes. Then, t-butyl 4-piperidinyloxyacetate (90 mg) in methylene chloride (2 ml) and diisopropylethylamine (0.14 ml) were added, and the solution was then stirred at room temperature for 3 hours. The reaction solution was diluted with ethyl acetate, washed with water, and then dried with magnesium sulfate. After the solvent was evaporated, the resultant residue was purified by silica gel column chromatography (30 g, chloroform:methanol=30:1) to give 170 mg of t-butyl [[1-[4-(1-t-butoxycarbonylpiperidin-4-yl)-2-oxopiperazin-1-yl]acetyl]piperidin-4-yl]oxyacetate.

$^1$H-NMR (CDCl$_3$) δ: 1.43 (2H, m), 1.46 (9H, s), 1.48 (9H, s), 1.69 (2H, m), 1.77–1.95 (4H, m), 2.44 (1H, m), 2.74 (2H, brt), 2.82 (2H, m), 3.23–3.45 (6H), 3.62–3.71 (2H, m), 3.84 (1H, m), 3.98 (1H, d, J=15.2 Hz), 4.02 (1H, d, J=15.2 Hz), 4.08 (1H, d, J=15.7 Hz), 4.12 (2H, brs), 4.31 (1H, d, J=15.7 Hz).

EIMS (m/z): 538 (M$^+$)

(d) The compound obtained in the above (c) was treated by the same procedure as in Example 1(c) to give the title compound.

$^1$H-NMR (D$_2$O) δ: 1.53–1.71 (2H, m), 1.97–2.10 (4H, m), 2.50 (2H, brd), 3.11–3.24 (4H, m), 3.31 (1H, m), 3.66–3.87 (8H), 4.00 (1H, m), 4.17 (2H, s), 4.28 (2H, s), 4.46 (2H, s).

SIMS (m/z): 383 (M$^+$+1)

EXAMPLE 3

[[4-[4-(piperidin-4-yl)piperazin-1-yl]acetyl]-o-phenylene]dioxy]diacetic acid trifluoroacetate (a) The same procedure as in Example 1(a) was repeated except that 1-t-butoxycarbonyl-4-oxopiperidine and 1-benzylpiperazine were used to give 1-benzyl-4-(1-t-butoxycarbonylpiperidin-4-yl)piperazine.

$^1$H-NMR (CDCl$_3$) δ: 1.38 (2H, m), 1.45 (9H, s), 1.80 (2H, brd), 2.35 (1H, m), 2.40–2.75 (10H), 3.50 (2H, s), 4.12 (2H, brs), 7.30 (5H, m).

EIMS (m/z): 359 (M$^+$)

(b) The compound (2.75 g) obtained in the above (a) was dissolved in methylene chloride (50 ml), and sodium hydrogencarbonate (1.91 g) was added and benzyl chloroformate (2.04 ml) was further added to the solution under ice-cooling. Then, the mixture was stirred at room temperature, and benzyl chloroformate was added in an amount of 0.8 ml after 4 hours and in an amount of 1.0 ml after 9 hours, followed by stirring overnight. The reaction solution was diluted with ethyl acetate, washed with water, and then dried over magnesium sulfate. After the solvent was evaporated, the residue was purified by silica gel column chromatography (120 g, chloroform→chloroform:ethyl acetate=1:4) to give 1-benzyloxycarbonyl-4-(1-t-butoxycarbonylpiperidin-4-yl)piperazine (2.88 g).

$^1$H-NMR (CDCl$_3$) δ: 1.39 (2H, m), 1.45 (9H, s), 1.77 (2H, brd), 2.40 (1H, m), 2.51 (4H), 2.69 (2H, brt), 3.51 (4H, m), 4.12 (2H, brs), 5.13 (2H, s), 7.37 (5H, m).

(c) The compound (1.0 g) obtained in the above (b) was dissolved in ethanol (5 ml), and a 1N ethanol-hydrochloric acid solution (5 ml) and palladium black (50 mg) were then added to the solution. Catalytic reduction was carried out under atmospheric pressure for 3 hours. After the used catalyst was removed by filtration, the filtrate was then concentrated. The resultant residue was dissolved in water, and the pH of the solution was adjusted to 8 with an ion exchange resin Amberlight IR-45 (OH$^-$). After the resin was removed by filtration, the filtrate was then concentrated. The resultant residue was purified by silica gel column chromatography (30 g, 1% triethylamine-containing chloroform:methanol=20:1→2% triethylamine-containing chloroform:methanol=10:1) to give 277 mg of 4-(1-t-butoxycarbonylpiperidin-4-yl)piperazine.

$^1$H-NMR (CDCl$_3$) δ: 1.40 (2H, m), 1.45 (9H, s), 1.76 (2H, brd), 2.46 (1H, m), 2.69 (2H, brt), 2.82 (4H, m), 3.17 (4H, m), 4.12 (2H, brs).

EIMS (m/z): 269 (M$^+$)

(d) The compound (135 mg) obtained in the above (c) was dissolved in DMF-(2 ml), and potassium carbonate (138 mg)

and di-t-butyl [(4-chloroacetyl-o-phenylene)dioxy]diacetate (275 mg) were added to the solution, followed by stirring at room temperature for 4 hours. The reaction solution was diluted with ethyl acetate, washed with water, and then dried over magnesium sulfate. After ethyl acetate was evaporated, the residue was purified by silica gel column chromatography (chloroform:methanol=40:1) to give 213 mg of di-t-butyl [[4-[4-(1-t-butoxycarbonylpiperidin-4-yl)piperazin-1-yl]acetyl]-o-phenylene]dioxy]diacetate.

$^1$H-NMR (CDCl$_3$) δ: 1.38 (2H, m), 1.45 (9H, s), 1.47 (9H, s), 1.48 (9H, s), 1.82 (2H, brd), 2.37 (1H, m), 2.55–2.76 (10H), 3.74 (2H, s), 4.13 (2H, brs), 4.64 (2H, s), 4.67 (2H, s), 6.80 (1H, d, J=8.5 Hz), 7.53 (1H, d, J=1.8 Hz), 7.64 (1H, dd, J=1.8, 8.5 Hz).

EIMS (m/z): 647 (M$^+$)

(e) The compound obtained in the above (d) was treated by the same procedure as in Example 1(c) to give the title compound.

$^1$H-NMR (D$_2$O) δ: 1.97 (2H, m), 2.46 (2H, brd), 3.15 (2H, brt), 3.51–3.72 (9H), 4.85 (2H, brs), 4.86 (2H, s), 4.87 (2H, s), 4.91 (2H, s), 7.10 (1H, d, J=8.6 Hz), 7.51 (1H, s), 7.69 (1H, d, J=8.6 Hz).

SIMS (m/z): 436 (M$^+$+1)

EXAMPLE 4

Diethyl [[4-[4-(piperidin-4-yl)-2-oxopiperazin-1-yl]acetyl]-o-phenylene]dioxy]diacetate The same procedure as in Example 1(b) and (c) was repeated except that di-t-butyl [(4-chloroacetyl-o-phenylene)dioxy]diacetate was replaced with diethyl[(4-chloroacetyl-o-phenylene)dioxy]diacetate to give the title compound.

$^1$H-NMR (D$_2$O) δ: 1.31 (3H, t, J=7 Hz), 1.32 (3H, t, J=7 Hz), 2.00 (2H, m), 2.47 (2H, brd), 3.18 (2H, brt), 3.55–3.76 (7H, m), 4.03 (2H, s), 4.33 (4H, q, J=7 Hz), 4.96 (2H, s), 5.01 (2H, s), 5.05 (2H, s), 7.14 (1H, d, J=8 Hz), 7.59 (1H, s), 7.79 (1H, d, J=8 Hz).

SIMS (m/z): 506 (M$^+$+1)

EXAMPLE 5

4-[4-(piperidin-4-yl)-2-oxopiperazin-1-yl]acetyl]phenoxyacetic acid

The same procedure as in Example 1(b) and (c) was repeated except that di-t-butyl [(4-chloroacetyl-o-phenylene)dioxy]diacetate was replaced with t-butyl 4-bromoacetylphenoxyacetate to give the title compound.

$^1$H-NMR (CD$_3$OD) δ: 1.85–1.95 (2H, m), 2.27–2.30 (2H, m), 3.05–3.11 (2H, m), 3.15–3.21 (1H, m), 3.40–3.42 (2H, m), 2.51–3.60 (4H, m), 3.72 (2H, s), 4.79 (2H, s), 4.93 (2H, s), 7.06 (2H, d, J=8.9 Hz), 8.01 (2H, d, J=8.9 Hz).

SIMS (m/z): 376 (M$^+$+1)

EXAMPLE 6

[[1-[4-(piperazin-4-yl)piperidin-1-yl]acetyl]piperidin-4-yl]oxyacetic acid trifluoroacetate The same procedure as in Example 2(b) and (c) was repeated except that [4-(1-t-butoxycarbonylpiperidin-4-yl)-2-oxopiperazin-1-yl]acetic acid hydrochloride was replaced with [4-(4-t-butoxycarbonylpeperazin-1-yl)piperidin-1-yl] acetic acid to give the title compound.

$^1$H-NMR (CD$_3$OD) δ: 1.60–1.73 (2H, m), 1.84–1.96 (3H, m), 2.10–2.20 (2H, m), 2.68–2.97 (4H, m), 3.05–3.30 (7H, m), 3.42–3.48 (2H, m), 3.55–3.62 (2H, m), 3.67–3.75 (2H, m), 3.80–3.90 (2H, m), 4.16 (2H, s), 4.24 (2H, s).

SIMS (m/z): 369 (M$^+$+1)

EXAMPLE 7 n-butyl 4-[[4-(piperidin-4-yl)-2,6-dioxopiperazin-1-yl]acetyl]phenoxyacetate hydrochloride (a) A mixture of 1-t-butoxycarbonyl-4-oxopiperidine (9.06 g) and 2,6-dioxopiperazine (3.99 g) was dissolved in 1,2-dichloroethane (170 ml), and acetic acid (20 ml) of triacetoxyboronsodium hydride (9.64 g) were added to the solution, followed by stirring at room temperature for 17 hours. Then, water was added to the reaction solution under ice-cooling, and sodium hydrogencarbonate was added to the solution to neutralize acetic acid. The reaction solution was charged into a separating funnel to separate an aqueous layer from an organic layer. The aqueous layer was extracted with chloroform, and the extracted organic layer was then combined with the above organic layer. The combined organic layer was washed with a saturated saline solution and then dried over sodium sulfate. After the solvent was evaporated, the residue was purified by silica gel column chromatography (350 g, chloroform→chloroform:methanol=60:1) to give a crystal. Then, n-hexane was added to the crystal, and the crystal was collected by filtration to give 6.46 g (62%) of 4-(1-t-butoxycarbonylpiperidin-4-yl)-2,6-dioxopiperazine.

$^1$H-NMR (CDCl$_3$) δ: 1.35–1.52 (11H), 1.77 (2H, brd), 2.58 (1H, tt, J=3.6, 11.4 Hz), 2.73 (2H, brt), 3.46 (4H, s), 4.15 (2H, brs), 8.02 (1H, s).

EIMS (m/z): 297 (M$^+$)

(b) The compound (3.57 g) obtained in the above (a) was dissolved in dimethylformamide (60 ml), and sodium hydride (about 60% oil suspension, 0.72 g) was added to the solution, followed by stirring for 10 minutes. To the reaction solution, n-butyl 4-bromoacetylphenoxyacetate (4.35 g) in dimethylformamide (25 ml) was added under ice-cooling, followed by stirring for 3 hours. Water was added to the reaction solution, and extracted with ethyl acetate. The extract was washed with water and a saturated saline solution, and then dried over sodium sulfate. After the solvent was evaporated, the residue was purified by silica gel column chromatography (250 g, hexane:ethyl acetate=1:1) to give 4.67 g (71%) of n-butyl 4-[[4-(1-t-butoxycarbonylpiperidin-4-yl)-2,6-dioxopiperazine-1-yl] acetyl]phenoxyacetate.

$^1$H-NMR (CDCl$_3$) δ: 0.93 (3H, t, J=7.4 Hz), 1.30–1.53 (13H), 1.56–1.70 (2H, m), 1.83 (H, brd), 2.64 (1H, tt, J=3.3, 11.3 Hz), 2.77 (2H, brt), 3.64 (4H, s), 4.16 (2H, brs), 4.22 (2H, t, J=6.7 Hz), 4.70 (2H, s), 5.14 (2H, s), 6.97 (2H, d, J=9.0 Hz), 7.95 (2H, d, J=9.0 Hz).

EIMS (m/z): 545 (M$^+$)

(c) To the compound (4.67 g) obtained in the above (b), anisole (7 ml), trifluoroacetic acid (20 ml) and methylene chloride (10 ml) were added, followed by stirring at room temperature for 1 hour. Water was added to the reaction solution, and neutralized with sodium hydrogencarbonate. After the solvent was evaporated, water was added to the residue, and extracted with ethyl acetate. The extract was dried over sodium sulfate, and the solvent was evaporated. The resultant residue was purified by silica gel column chromatography (200 g, chloroform:methanol=10:1 to 7:1) to give a light yellow crystal (4.15 g). This crystal was used in the hydrolytic reaction of the following Example 8. On the other hand, to this crystal (1.02 g), n-butanol (6 ml) and chloroform (18 ml) were added, and the solution was then stirred for 20 minutes under ice-cooling, while a hydrochloric acid gas was blown into the solution. After stirring at room temperature for additional 1 hour, the solvent was evaporated. After ether was added to the resultant residue, the crystal was then collected by filtration to give 0.618 g (52%) of the title compound.

$^1$H-NMR (D$_2$O) δ: 0.76–0.85 (3H, m), 1.16–1.29 (2H, m), 1.50–1.62 (2H, m), 1.65–1.79 (2H, m), 2.16 (2H, brd), 2.94–3.10 (3H), 3.52 (2H, brd), 3.74–3.87 (4H, m), 4.15–4.23 (2H, m), 4.80–4.89 (2H, m), 5.20–5.28 (2H, m), 6.90–7.09 (2H, m), 7.93–8.03 (2H, m).

EIMS (m/z): 445 (M$^+$)

EXAMPLE 8

4-[[4-(piperidin-4-yl)-2,6-dioxopiperazin-1-yl]acetyl]phenoxyacetic acid hydrochloride To the light yellow crystal (0.312 g) obtained in Example 7(c), 5N hydrochloric acid (7 ml) was added under ice-cooling, and the solution was then stirred for 16 hours, while heated up to room temperature. After the solvent was evaporated, the resultant residue was purified by an HP column (150 ml, water-5% aqueous acetone), and then lyophilized to give 0.103 g (35%) of the title compound.

$^1$H-NMR (D$_2$O) δ: 2.57–2.73 (2H, m), 2.10 (2H, brd), 2.84–3.03 (3H), 3.45 (2H, brd), 3.74 (4H, s), 4.50 (2H, s), 5.21 (2H, s), 6.96 (2H, d, J=8.8 Hz), 7.94 (2H, d, J=8.8 Hz).

EIMS (m/z): 389 (M$^+$)

EXAMPLE 9 n-butyl 4-[[4-(piperidin-4-yl)-2,3-dioxopiperazin-1-yl]acetyl]phenoxyacetate hydrochloride (a) The same procedure as in Example 1(a) was repeated except that 2,6-dioxopiperazine was replaced with N-benzyloxycarbonylethylenediamine hydrochloride to give 14.7 g (87%) of N-benzyloxycarbonyl-N'-(1-t-butoxycarbonylpiperidin-4-yl)ethylenediamine.

$^1$H-NMR (CDCl$_3$) δ: 1.13–1.27 (2H, m), 1.45 (9H, s), 1.81 (2H, brd), 2.52–2.63 (1H, m), 2.44 (1H, m), 2.74 (2H, brt), 2.82 (2H, m), 2.70–2.86 (4H, m), 3.22–3.33 (2H, m), 4.00 (2H, brs), 5.10 (2H, s), 5.19 (1H, brs), 7.29–8.29 (5H, m).

EIMS (m/z): 377 (M$^+$)

(b) The compound (10.6 g) obtained in the above (a) was dissolved in methylene chloride (140 ml), and triethylamine (4.7 ml) was added to the solution. Then, ethyl chloroglyoxylate (3.1 ml) was added thereto under ice-cooling, followed by stirring for 30 minutes. To the reaction solution, water (140 ml) was added under ice-cooling, and the reaction solution was charged into a separating funnel to separate an aqueous layer from an organic layer. The aqueous layer was extracted with chloroform, and the extracted organic layer was then combined with the above organic layer. The combined organic layer was washed with water, a saturated sodium bicarbonate solution and a saturated saline solution, and then dried over magnesium sulfate. After the solvent was evaporated, the residue was purified by silica gel column chromatography (300 g, hexane:ethyl acetate=2:1 to 3:2) to give 12.3 g (93%) of ethyl N-2-(benzyloxycarbonylamino)ethyl-N-(1-t-butoxycarbonylpiperidin- 4-yl)aminoglyoxylate.

$^1$H-NMR (CDCl$_3$) δ: 1.36 (3H, t, J=7.2 Hz), 1.47 (9H, s), 1.69–1.83 (4H, m), 2.55–2.82 (2H, m), 3.37–3.50 (5H), 4.09–4.30 (2H, m), 4.36 (2H, q, J=7.2 Hz), 5.10 (2H, s), 5.21 (1H, brs), 7.35 (5H, s).

FDMS (m/z): 478 (M$^+$+1)

(c) The compound (8.12 g) obtained in the above (b) was dissolved in ethanol (85 ml), and 10% palladium-carbon (270 mg) was added to the solution, followed by catalytic reduction under atmospheric pressure for 4 hours. After the catalyst was removed by filtration, the solvent was evaporated to give 6.76 g of 4-(1-t-butoxycarbonylpiperidin-4-yl)-2,3-dioxopiperazine. This product was used in a subsequent reaction without purification.

$^1$H-NMR (CD$_3$OD) δ: 1.46 (9H, s), 1.60–1.74 (4H, m), 2.86 (2H, brs), 3.41–3.47 (2H, m), 3.49–3.55 (2H, m), 4.20 (2H, brd), 4.43–4.53 (1H, m).

EIMS (m/z): 297 (M$^+$)

(d) The same procedure as in Example 7(b) was repeated except that 4-(1-t-butoxycarbonylpiperidin-4-yl)-2,6-dioxopiperazine was replaced with the compound obtained in the above (c) to give 2.59 g of n-butyl 4-[[4-(1-t-butoxycarbonylpiperidin-4-yl)-2,3-dioxopiperazin-1-yl]acetyl]phenoxyacetate. (The yield of the product from the compound obtained in the above (b) was 59%.)

$^1$H-NMR (CDCl$_3$) δ: 0.93 (3H, t, J=7.4 Hz), 1.36 (2H, m), 1.47 (9H, s), 1.54–1.70 (4H), 1.74 (2H, brd), 2.83 (2H, brt), 3.51–3.62 (4H, m), 4.15–4.32 (4H), 4.66 (1H, tt, J=3.4, 12.8 Hz), 4.71 (2H, s), 4.93 (2H, s), 6.97 (2H, d, J=9.0 Hz), 7.94 (2H, d, J=9.0 Hz).

FDMS (m/z): 545 (M$^+$)

(e) The compound obtained in the above (d) was treated by the same procedure as in Example 1(c) to give 0.298 g (52%) of the title compound.

$^1$H-NMR (D$_2$O) δ: 0.82 (3H, t, J=7.3 Hz), 1.25 (2H, m), 1.58 (2H, m), 1.97–2.07 (4H, m), 3.07–3.19 (2H, m), 3.54 (2H, brd), 3.67 (4H, s), 4.21 (2H, t, J=6.5 Hz), 4.45–4.54 (1H, m), 4.86 (2H, s), 5.02 (2H, s), 7.05 (2H, d, J=9.2 Hz), 7.97 (2H, d, J=9.2 Hz).

SIMS (m/z): 446 (M$^+$+1)

EXAMPLE 10

4-[[4-(piperidin-4-yl)-2,3-dioxopiperazin-1-yl]acetyl]phenoxyacetic acid.hydrochloride The compound obtained in Example 9 was treated by the same procedure as in Example 8 to give 0.211 g (68%) of the title compound.

$^1$H-NMR (CF$_3$COOD) δ: 2.25–2.34 (2H, m), 2.36–2.51 (2H, m), 3.40–3.54 (2H, m), 3.81–4.01 (6H), 4.87 (1H, brt), 4.97 (2H, s), 5.23 (2H, s), 7.17 (2H, d, J=8.8 Hz), 7.38 (1H, brs), 8.11 (2H, d, J=8.8 Hz).

SIMS (m/z): 390 (M$^+$+1)

EXAMPLE 11 n-butyl 4-[[4-piperidin-4-yl)-2,5-dioxopiperazin-1-yl]acetyl]phenoxyacetate.trifluoroacetate (a) The same procedure as in Example 7(a) was repeated except that 2,6-dioxopiperazine was replaced with glycine ethyl ester hydrochloride to give 9.79 g (86%) of ethyl (1-t-butoxycarbonylpiperidin-4-yl)aminoacetate.

$^1$H-NMR (CD$_3$OD) δ: 1.19–1.31 (5H), 1.45 (9H, s), 1.86 (2H, brd), 2.62–2.71 (1H, m), 2.80 (2H, brs), 3.43 (2H, s), 4.04 (2H, brd), 4.19 (2H, q, J=7.2 Hz).

EIMS (m/z): 286 (M$^+$)

(b) The compound (9.38 g) obtained in the above (a) was dissolved in dimethylformamide (100 ml), and benzotriazole-1-yloxytris(dimethylamino)phosphonium hexafluorophosphate (26.1 g) and N-methylmorpholine (7.6 ml) were added to the solution, followed by stirring at room temperature for 2 hours. To the reaction solution, N-benzyloxycarbonylglycine (6.86 g) in dimethylformamide (60 ml) was added at room temperature, and the solution was then further stirred for 19 hours. Then, 0.2N hydrochloric acid was added to the reaction solution under ice-cooling, and the reaction solution was charged into a separating funnel to separate an aqueous layer from an organic layer. The aqueous layer was extracted with chloroform, and the extracted organic layer was then combined with the above organic layer. The combined organic layer was washed with water, a saturated sodium bicarbonate solution and a saturated saline solution, and then dried over sodium sulfate. After the solvent was evaporated, ethyl acetate was added to the residue, and a precipitated crystal was removed by filtration. The filtrate was concentrated, and the resultant residue was purified by silica gel column chromatography (350 g, hexane:ethyl acetate=2:1) to give 14.4 g (92%) of ethyl N-(benzyloxycarbonylaminoacetyl)-N-(1-t-butoxycarbonylpiperidin-4-yl)aminoacetate.

$^1$H-NMR (CDCl$_3$) δ: 1.24–1.55 (13H), 1.62–1.81 (4H, m), 2.65–2.84 (2H, m), 3.61–3.7, 4.57–4.67 (1H, 2×m), 3.86–4.00 (3H), 4.05–4.32 (5H), 5.12, 5.13 (2H, 2×s), 5.73, 5.80 (1H, brs), 7.28–7.39 (5H, m).

SIMS (m/z): 478 (M$^+$+1)

(c) The compound obtained by the above (b) was treated by the same manner as in Example 9(c), and recrystallized with ethyl acetate to give 6.31 (85%) of 4-(1-t-butoxycarbonylpiperidin-4-yl)-2,5-dioxopiperazine.

$^1$H-NMR (CDCl$_3$) δ: 1.42–1.70 (13H), 2.80 (2H, brt), 3.86 (2H, s), 4.23 (2H, brs), 4.58 (1H, tt, J=4.4, 11.8 Hz), 6.41 (1H, brs).

EIMS (m/z): 297 (M$^+$)

(d) The compound obtained in the above (c) was allowed to react in the same manner as in Example 7(b), and acetic acid (0.9 ml) was then added to the reaction solution under ice-cooling, followed by stirring for 15 minutes. Then, water was added thereto under ice-cooling to terminate the reaction and extracted with ethyl acetate. The extract was washed with water, a saturated sodium bicarbonate solution and a saturated saline solution, and then dried over sodium sulfate. After the solvent was evaporated, the residue was purified by silica gel column chromatography (150 g, chloroform:methanol=100:1). Then, ether was added to the resultant crystal, and the crystal was then collected by filtration to give 2.11 g (70%) of n-butyl 4-[[4-(1-t-butoxycarbonylpiperidin-4-yl)-2,5-dioxopiperazin-1-yl]acetyl]phenoxyacetate.

$^1$H-NMR (CDCl$_3$) δ: 0.93 (3H, t, J=7.4 Hz), 1.36 (2H, m), 1.47 (9H, s), 1.54–1.72 (6H), 2.81 (2H, brt), 3.98 (2H, s), 4.10 (2H, s), 4.16–4.35 (4H), 4.60 (1H, tt, J=4.1, 11.8 Hz), 4.70 (2H, s), 4.79 (2H, s), 6.97 (2H, d, J=8.7 Hz), 7.93 (2H, d, J=8.7 Hz).

EIMS (m/z): 545 (M$^+$)

(e) To the compound (1.91 g) obtained in the above (d), anisole (3.5 ml) and trifluoroacetic acid (14 ml) were added under ice-cooling, followed by stirring at room temperature for 1.5 hours. Then, isopropyl ether was added to the reaction solution under ice-cooling. After the solvent was decanted, ether was added so as to cause crystallization. The resultant crystal was collected by filtration, washed with isopropyl ether and ether, and then dried to give 2.11 g (70%) of the title compound.

$^1$H-NMR (CD$_3$OD) δ: 0.93 (3H, t, J=7.4 Hz), 1.37 (2H, m), 1.60–1.69 (2H, m), 1.96–2.16 (4H, m), 3.09–3.19 (2H, m), 3.52 (2H, brd), 4.09 (2H, s), 4.12 (2H, s), 4.21 (2H, t, J=6.6 Hz), 4.50 (1H, tt, J=3.9, 11.7 Hz), 4.84 (2H, s), 4.92 (2H, s), 7.05 (2H, d, J=9.0 Hz), 8.00 (2H, d, J=9.0 Hz).

EIMS (m/z): 445 (M$^+$)

EXAMPLE 12

4-[[4-(piperidin-4-yl)-2,5-dioxopiperazin-1-yl]acetyl]phenoxyacetic acid hydrochloride The compound obtained in Example 11 was treated by the same procedure as in Example 8 to give 0.417 g (98%) of the title compound.

$^1$H-NMR (D$_2$O) δ: 1.92–2.01 (4H, m), 3.05–3.17 (2H, m), 3.53 (2H, brd), 4.11 (4H, s), 4.45–4.55 (1H, m), 4.58 (2H, s), 4.91 (2H, s), 7.00 (2H, d, J=8.8 Hz), 7.93 (2H, d, J=8.8 Hz).

SIMS (m/z): 390 (M$^+$+1)

EXAMPLE 13 n-butyl 4-[[4-(piperidin-4-yl)-2-oxopiperazin-1-yl]acetyl]phenoxyacetate dihydrochloride The same procedure as in Example 4 was repeated except that n-butyl (4-bromoacetyl)phenoxyacetate was used to give the title compound.

$^1$H-NMR (CD$_3$OD) δ: 8.00 (2H, d, J=9.0 Hz), 7.04 (2H, d, J=9.0 Hz), 4.87 (2H, s), 4.82 (2H, s), 4.21 (2H, t, J=6.7 Hz), 3.48–3.42 (4H, m), 3.32–3.30 (2H, m), 3.04 (2H, dt, J=2.7 Hz, J=2.3 Hz), 2.93 (2H, t, J=5.5 Hz), 2.71 (1H, ddd, J=3.5 Hz, J=6.7 Hz, J=13.8 Hz), 2.15–2.10 (2H, m), 1.83–1.73 (2H, m), 1.67–1.60 (2H, m), 1.37 (2H, dt, J=7.4 Hz, J=14.9 Hz), 0.93 (3H, t, J=7.4 Hz).

EXAMPLE 14 ethyl 4-[[4-(piperidin-4-yl)-2-oxopiperazin-1-yl]acetyl]phenoxyacetate

The same procedure as in Example 4 was repeated except that ethyl (4-bromoacetyl)phenoxyacetate was used to give the title compound.

$^1$H-NMR (CD$_3$OD) δ: 1.28 (3H, t, J=7.2 Hz), 1.80–1.90 (2H, m), 2.20–2.27 (2H, m), 3.02–3.10 (3H, m), 3.20–3.23 (2H, m), 3.49–3.57 (4H, m), 3.61 (2H, bds), 4.25 (2H, q, J=7.2 Hz), 4.82 (2H, s), 4.91 (2H, s), 7.04 (2H, d, J=8.9 Hz), 8.00 (2H, d, J=8.9 Hz).

SIMS (m/z): 404 (M$^+$+1)

EXAMPLE 15 ethyl 4-[[4-[1-(5-methyl-2-oxodioxol-4-yl)methylpiperidin-4-yl]-2-oxopiperazin-1-yl]acetyl]phenoxyacetate The compound obtained in Example 14 (150 mg) was dissolved in 5 ml of anhydrous DMF, and 98 mg of potassium carbonate and 55 mg of 4-bromomethyl-5-methyl-2-oxodioxol were added to the solution, followed by stirring at room temperature for 1.5 hours. Then, the reaction solution was diluted with ethyl acetate, washed twice with water, and then dried over magnesium sulfate. An inorganic salt was removed by filtration, and the filtrate was concentrated under reduced pressure. The resultant oil was purified by silica gel column chromatography (dichloromethane:methanol=20:1). The resultant substance was dissolved in 1,4-dioxane, and 1N HCl was added thereto. The solution was lyophilized overnight to give 58 mg (yield 40%) of the title compound.

$^1$H-NMR (CDCl$_3$) δ: 1.30 (3H, t, J=7.2 Hz), 1.57–1.65 (2H, m), 1.83–1.86 (2H, m), 2.08–2.15 (2H, m), 2.11 (3H, s), 2.29–2.36 (1H, m), 2.83–2.86 (2H, m), 2.92–2.94 (2H, m), 3.32 (2H, s), 3.36–3.38 (4H, m), 4.28 (2H, q, J=7.2 Hz), 4.69 (2H, s), 4.77 (2H, s), 6.95 (2H, d, J=8.6 Hz), 7.95 (2H, d, J=8.6 Hz).

FD (m/z): 515 (M$^+$)

EXAMPLE 16

3-[4-[[4-(piperidin-4-yl)-2-oxopiperazin-1-yl]acetyl]phenyl]propionic acid trifluoroacetate The same procedure as in Example 1(b) and (c) was repeated except that diphenylmethyl 3-(4-chloroacetyl)phenylpropionate was used to give the title compound.

$^1$H-NMR (D$_2$O) δ: 1.75–1.83 (2H, m), 2.29–2.33 (2H, m), 2.74 (2H, t, J=7 Hz), 3.03–3.21 (7H, m), 3.55–3.77 (6H, m), 5.02 (2H, s), 7.49 (2H, d, J=8 Hz), 7.98 (2H, d, J=8 Hz).

MS (m/z): 373 (M$^+$)

The structures of compounds obtained in Examples are as follows. The numbers of the compounds correspond to those of the examples.

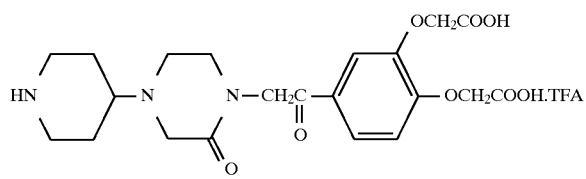

(1)

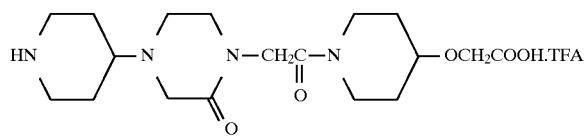

(2)

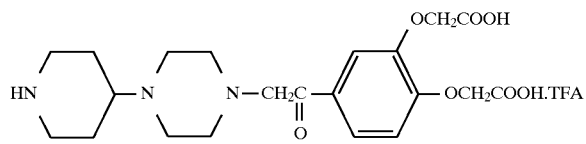

(3)

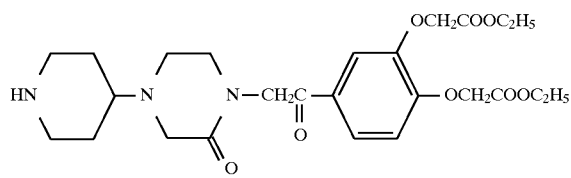

(4)

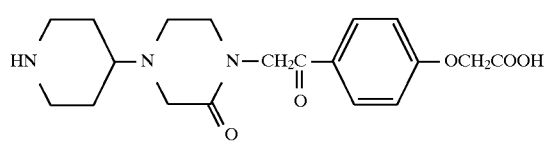

(5)

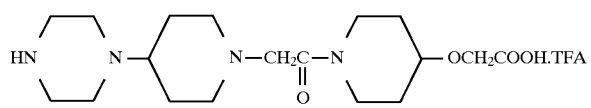

(6)

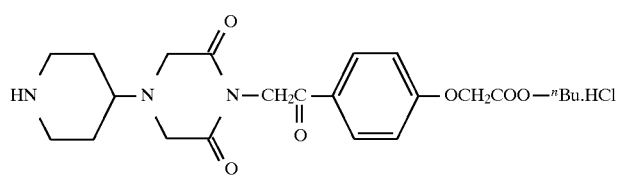

(7)

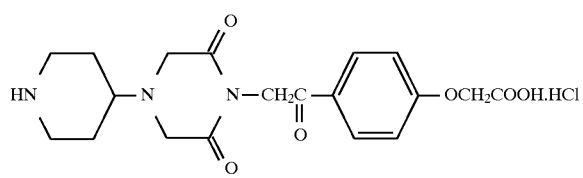

(8)

-continued

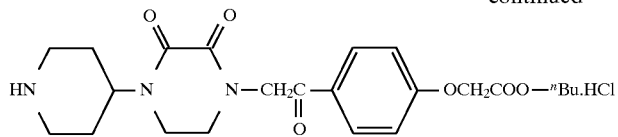
(9)

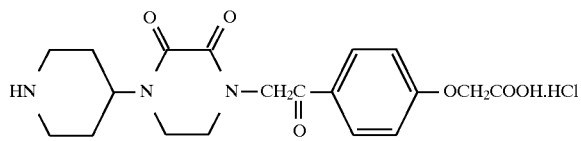
(10)

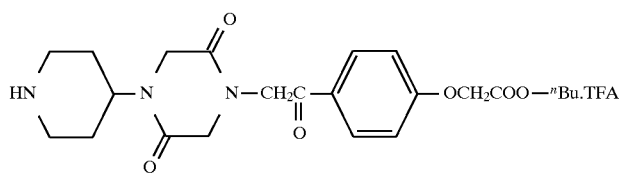
(11)

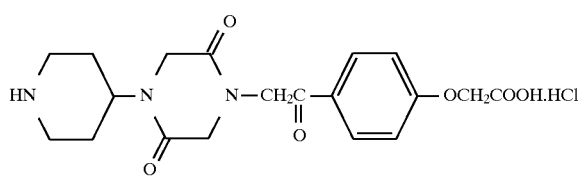
(12)

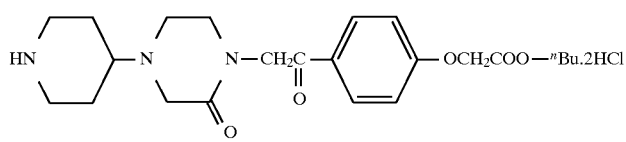
(13)

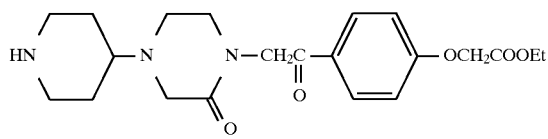
(14)

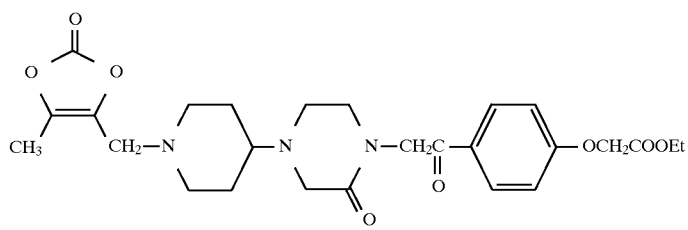
(15)

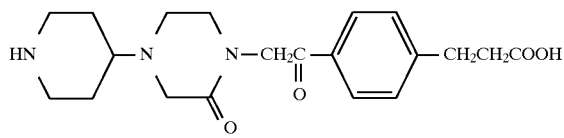
(16)

Pharmacological test: Inhibition of platelet aggregation

The effect of the compound according to the present invention on inhibiting the platelet aggregation was examined with human PRP (platelet rich plasma).

Nine volumes of a blood sample was taken out of the vein of a normal male human with a syringe in which one volume of a 3.8% sodium citrate solution was charged. The blood sample was centrifuged at 170×g at room temperature for 10 minutes. The supernatant thus obtained was isolated as PRP. The residual blood sample that PRP had been taken out was centrifuged at 2,700×g for 15 minutes. The supernatant was then taken as platelet poor plasma (PPP).

Platelet aggregation test was conducted with an aggligometer (PAM-8C; manufactured by MEBANICKS Co., Ltd.). Compounds to be tested were dissolved in a 50% DMSO saline, a 50% methanol saline or physiological saline. The compound and PRP were preincubated for 2 minutes. The ADP (CHRONO-PAR REAGENTS 384 ADP, CHRONO-LOG Corp.) was used as an inducer in the form of a dilution with saline so that the final concentration is 5 $\mu$M.

Anti-platelet aggregation activity was obtained as an inhibition rate to platelet aggregation effect of ADP in the absence of a compound to be tested as follows:

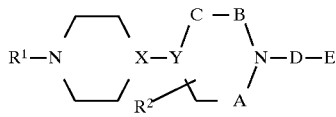

TABLE 1

| Example No. | IC$_{50}$ ($\mu$M) |
|---|---|
| 1 | 0.055 |
| 2 | 0.08 |
| 3 | 0.15 |
| 4 | 0.56 |
| 5 | 0.032 |
| 6 | 2.3 |
| 7 | 0.24 |
| 8 | 0.019 |
| 9 | 1.2 |
| 10 | 0.47 |
| 11 | 1.1 |
| 12 | 1.2 |
| 13 | 0.049 |
| 14 | 0.25 |
| 15 | 0.3 |
| 16 | 0.42 |

What is claimed is:

1. A compound represented by the following formula:

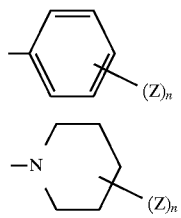

wherein A, B and C represent independently $CH_2$ or C=O;
X and Y are different from each other, and each of them is CH or N;
D is —$(CH_2)_k$— or —$(CH_2)_m$—CO— where k is an integer of 1 to 4; and m is an integer of 0 to 3;
E is the following group (II) or (III):

(II)

(III)

wherein n is an integer of 1 to 3; and Z is —W—$(CH_2)_p$—COOR$^3$ wherein W is —O— or a bond; p is an integer of 1 to 4; and R$^3$ is hydrogen, lower alkyl or an ester residue selected from the group consisting of pivaloyloxymethyl, 1-(cyclohexyloxycarbonyloxy)ethyl and (5-methyl-2-oxo-1,3-dioxol-4-yl)methyl;

R$^1$ is hydrogen; lower alkyl in which at least one hydrogen atom may be substituted by hydroxyl, halogen, amino, lower alkylamino, or lower-alkyl-substituted-2-oxodioxol-4-yl group; or lower alkyl in which two hydrogen atoms may be substituted by an imino group;

R$^2$ is hydrogen atom; lower alkyl in which at least one hydrogen atom may be substituted by hydroxyl, halogen, amino, carboxyl, lower alkoxy, lower alkylamino or lower alkoxycarbonyl; phenyl in which at least one hydrogen atom may be substituted by hydroxyl, halogen, amino, carboxyl, lower alkoxy, lower alkylamino, lower alkoxycarbonyl or halo-lower alkyl; or phenyl-lower alkyl in which at least one hydrogen atom of the phenyl group may be substituted by hydroxyl, halogen, amino, carboxyl, lower alkoxy, lower alkylamino, lower alkoxycarbonyl or halo-lower alkyl; or a pharmaceutically acceptable salt or solvate thereof.

2. The compound according to claim 1, wherein X is CH and Y is N.

3. The compound according to claim 1, wherein A is C=O and B and C are $CH_2$, or two of A, B and C each is C=O and the other is $CH_2$.

4. The compound according to claim 1, wherein D is —$(CH_2)_m$—CO—.

5. The compound according to claim 4, wherein m is an integer of 1 to 3.

6. The compound according to claim 1, wherein Z is —W—$(CH_2)_p$—COOR$^3$ wherein W is —O—.

7. The compound according to claim 1 selected from the group consisting of:
[[4-[[4-(piperidin-4-yl)-2-oxopiperazin-1-yl]acetyl]-o-phenylene]dioxy]diacetic acid,
[[4-[[4-(piperidin-4-yl)piperazin-1-yl]acetyl]-o-phenylene]dioxy]diacetic acid,
4-[[4-(piperidin-4-yl)-2-oxopiperazin-1-yl]acetyl]phenoxyacetic acid,
diethyl [[4-[[4-(piperidin-4-yl)-2-oxopiperazin-1-yl]acetyl]-o-phenylene]dioxy]diacetate,
n-butyl 4-[[4-(piperidin-4-yl)-2,6-dioxopiperazin-1-yl]acetyl]phenoxyacetate,
4-[[4-(piperidin-4-yl)-2,6-dioxopiperazin-1-yl]acetyl]phenoxyacetic acid,
n-butyl 4-[[4-(piperidin-4-yl)-2,3-dioxopiperazin-1-yl]acetyl]phenoxyacetate,
4-[[4-(piperidin-4-yl)-2,3-dioxopiperazin-1-yl]acetyl]phenoxyacetic acid,
n-butyl 4-[[4-(piperidin-4-yl)-2,5-dioxopiperazin-1-yl]acetyl]phenoxyacetate,
4-[[4-(piperidin-4-yl)-2,5-dioxopiperazin-1-yl]acetyl]phenoxyacetic acid,
n-butyl 4-[[4-(piperidin-4-yl)-2-oxopiperazin-1-yl]acetyl]phenoxyacetate.dihydrochloride and
ethyl 4-[[4-(piperidin-4-yl)-2-oxopiperazin-1-yl]acetyl]phenoxyacetate.

8. A pharmaceutical composition comprising an effective amount of the compound according to claim 1 or a pharmacologically acceptable salt or solvate thereof together with a pharmaceutically acceptable carrier.

9. A method for treatment or prophylaxis of a thrombotic disease by inhibition of platelet aggregation, comprising the step of administering to a mammal an effective amount of the compound according to claim 1.

10. A method for treatment or prophylaxis of the thrombotic disease according to claim 9, wherein the thrombotic disease is cerebral infarction, cardiac infarction, angina pectoris or peripheral arterial atresia.

* * * * *